United States Patent [19]

De Clippeleir et al.

[11] Patent Number: 4,962,265
[45] Date of Patent: Oct. 9, 1990

[54] PROCESS AND CATALYST FOR THE CATALYTIC DEHYDROGENATION OF HYDROCARBONS

[75] Inventors: Georges E. M. J. De Clippeleir, Sint-Pieters-Leeuw, Belgium; Elizabeth B. Ofstad, Jar; Steinar Kvisle, Oslo, both of Norway

[73] Assignee: Labofina, S.A., Brussels, Belgium

[21] Appl. No.: 310,261

[22] Filed: Feb. 13, 1989

[30] Foreign Application Priority Data

Feb. 11, 1988 [BE] Belgium ................................ 8800157
Feb. 11, 1988 [BE] Belgium ................................ 8800158

[51] Int. Cl.$^5$ .............................................. C07C 5/333
[52] U.S. Cl. ...................................... 585/660; 585/661
[58] Field of Search ................................ 585/660, 661

[56] References Cited

U.S. PATENT DOCUMENTS 4,551,574 11/1985 Imai et al. ............................. 585/660
4,880,764 11/1989 Imai et al. ............................. 585/660

*Primary Examiner*—Curtis R. Davis
*Attorney, Agent, or Firm*—Jim Wheelington; John K. Abokhair; M. Norwood Cheairs

[57] ABSTRACT

A process is described for the catalytic dehydrogenation of paraffinic hydrocarbons preferably having from 3 to 6 carbon atoms in the presence of a catalyst containing at least one metal of the platinum group, a co-catalyst and a promoter, the noble metal of the platinum group being deposited into the alumina support in two steps, the first one being followed by a calcination and a reduction, the second one being followed by a calcination.

8 Claims, No Drawings

PROCESS AND CATALYST FOR THE CATALYTIC DEHYDROGENATION OF HYDROCARBONS

BACKGROUND OF THE INVENTION

The present invention relates to a process for the catalytic dehydrogenation of hydrocarbons, such as paraffinic hydrocarbons. More dehydrogenation particularly, the present invention concerns an improved process for the dehydrogenation of paraffinic hydrocarbons having from 3 to 6 carbon atoms. The present invention also relates to the catalyst used to carry out the process.

The catalytic dehydrogenation of hydrocarbons has been possible for many years and constitutes an important catalytic process in view of the increasing demand for dehydrogenated products which are of valuable use in various forms, such as gasolines having a high octane number, plastic materials and synthetic rubbers.

Moreover, in view of the increasing production of LPG (liquified petroleum gas), it seems particularly interesting to be able to convert a part of those paraffinic hydrocarbons into dehydrogenated products such as propylene which is of particular interest for the manufacture of plastic materials.

The catalytic dehydrogenation of hydrocarbons is generally carried out in the presence of catalytic compositions containing platinum deposited on a support. The catalytic compositions can also contain other catalytically active metals such as tin or indium and promoters based on alkaline or alkali-earth metals.

Such processes and catalytic compositions have been described e.g. in U.S Pat. Nos. 2,479,209, 2,602,772, 2,930,763, 3,531,543, 3,745,112, 3,892,657, 3,909,451 or still in U.S. Pat. Nos. 4,329,258, 4,363,721 and 4,430,517.

Further, in most of these patents, it is also taught to use a halogen in order to improve the yield of the dehydrogenation reaction.

However, when the developed processes are applied to the dehydrogenation of propane, the yield of the reaction at 600° C. does not exceed about 30 to 35%. This amount is 70 to 81% of the total theoretical conversion, taking into account the thermodynamic constraints.

There is, therefore, a need to provide a process for the dehydrogenation of paraffinic hydrocarbons with improved yields.

OBJECT OF THE INVENTION

The object of the present invention is to provide an improved process for the dehydrogenation of hydrocarbons.

Another object of the present invention is to provide an improved dehydrogenation catalyst.

A more specific object of the present invention is to provide an improved process for the dehydrogenation of paraffinic hydrocarbons having from 3 to 6 carbon atoms in the presence of a catalyst containing a platinum group metal, a tin group metal and a promoter.

Another object of the present invention is to provide an improved process for the dehydrogenation of propane into propylene in the presence of an improved catalyst containing a platinum group metal, a tin group metal, and an alkali or alkaline-earth metal type promoter.

SUMMARY OF THE INVENTION

The process of the present invention comprises the catalytic dehydrogenation of paraffinic hydrocarbons in the presence of a catalyst, a co-catalyst and a promoter wherein the co-catalyst contains at least one group IV A metal, the promoter is selected from alkali metals and alkaline-earth metals and the catalyst is prepared by depositing a group VIII B metal on a suitable support in two steps, the first step being followed by calcination and reduction and the second step being followed by calcination.

DETAILED DESCRIPTION OF THE INVENTION

The process of the present invention more preferably entails the catalytic dehydrogenation of paraffinic hydrocarbons having from 3 to 6 carbon atoms by passing the paraffinic hydrocarbon over a catalyst containing an alumina support at least one group VIII B metal together with a group IV A metal co-catalyst and at least one alkali metal or alkaline-earth metal promoter. The dehydroqenation process is preferably carried out in the presence of the catalyst at a temperature between 400° and 800° C., under a pressure between about 0.001 and 10 atm and at a weight hourly space velocity between about 0.1 and 21.

The catalyst contains a catalytically effective amount of at least one metal from the platinum (VIII B) group (preferably from about 0.1 to 2% by weight) a catalytically effective mount of at least one metal from the tin (IV A) group as co-catalyst (preferably about 0.1 to 2% by weight) and an effective amount of at least one alkali or alkaline-earth metal as promoter (preferably about 0.5 to 5% by weight.)

The catalyst is prepared by submitting the support containing the co-catalyst:

to a first treatment with a metal compound of the platinum group, followed by a calcination in air and by a reduction in the presence of hydrogen preferably at a temperature between about 450° and 550° C.;

then to an intermediate treatment to deposit the promoter, followed by a calcination, preferably at a temperature between about 380° and about 550° C.;

and finally to a second treatment with a metal compound of the platinum group, followed by a calcination preferably at a temperature not exceeding 525° C., It is preferred that the support be alumina and that the support and co-catalyst be calcined prior to being submitted to the first treatment (preferably at a temperature between about 450° and 550° C.).

The process of the present invention can be applied to the dehydrocyclization of hydrocarbons having at least 6 carbon atoms but is more preferably applied to the dehydroqenation of paraffinic hydrocarbons having from 3 to 6 carbon atoms, and particularly to the dehydrogenation of propane and butanes.

The Applicants have unexpectedly found that by applying the process of the invention using the inventive catalyst it becomes possible to considerably increase the yield of the dehydrogenation reaction when compared to the thermodynamic equilibrium, said yield being apt to exceed 90% of theoretical yield when propane is dehydrogenated at a temperature of about 600° C.

The metal of the platinum group, as used herein, is preferably selected from the group consisting of platinum, palladium, rhenium, iridium, rhodium, osmium, ruthenium or mixtures thereof, platinum being most preferred. The metal of the tin group, as used herein, is preferably selected from the group consisting of tin, germanium, lead or mixtures thereof, tin being most preferred, which may be present as a compound such as the oxide. The promoter can be an alkali metal selected from the group consisting of cesium, rubidium, potassium, sodium, lithium or mixtures thereof, or an alkaline-earth meta) selected from the group consisting of barium, strontium, calcium, magnesium or mixtures thereof, or even mixtures of alkali and alkaline-earth metals, potassium being preferred; other promoters known generally to be efficient are also envisaged as being useful for the present invention.

When alumina is used as support it generally has a specific area between about 150 and 350 $m^2/g$ and a pore volume comprised between about 0.2 and 1.2 ml/g.

It is also preferable to use an alumina having a purity higher than 98.5%, and in which the silica content does not exceed 1% while the iron content is lower than 0.1%.

The Applicants have unexpectedly found that the manner and the particular sequence of introduction of the catalytic metal compounds on the support, together with the conditions of intermediate calcination have an important influence on the catalyst activity in the scope of a dehydrogenation reaction.

The Applicants have found that by applying the following sequence for the treatment of the alumina support, a particularly suitable catalyst is obtained for use in the dehydrogenation process of the present invention.

The alumina support is first impregnated with a compound of the metal of the tin group, in order to obtain a preferred concentration of said metal in the final catalyst between 0.1 and 2% by weight more preferably between about 0.15 and 1.0% by weight.

As metal of the tin group, it is preferable to use tin. According to a preferred embodiment of the invention, a slurry is formed from alumina and an aqueous solution of tin chloride. The slurry is then dried preferably at a temperature of about 80° to 100° C. during 12 to 20 hours.

The so-formed support is then treated so as to introduce therein a metal compound of the platinum group. According to the present invention, the support is treated so as to deposit thereon in a first step, a small fraction of the total metal of the platinum group which has to be finally present. Preferably the amount of the platinum group metal deposited at this stage is between about 10% and 40% of the total amount of the platinum group metal. The deposition of this metal can be carried out by means of any suitable technique such as impregnation. When platinum is to be deposited, the support is preferably impregnated with an aqueous solution of chloroplatinic acid. After this impregnation, the newly impregnated support is submitted to a calcination preferably at a temperature between about 450° and 550° C. during 15 to 20 hours.

Thereafter, the calcined support is submitted to a reduction under hydrogen atmosphere also preferably at a temperature between about 450° and 550° C., during from about 1 to 4 hours.

The Applicant has found that this reduction step is very important and has a beneficial effect on the yield during the dehydrogenation of paraffinic hydrocarbons in the presence of this catalyst.

Before carrying out a second treatment with the platinum group metal, the support is submitted to an intermediate treatment with a promoter.

The alkali or alkaline-earth metal is preferably well dispersed on the support. The amount of alkali or alkaline-earth metal compound present on the support is preferably between about 0.5 and about 5% by weight more preferably between about 0.8 and 2.5% by weight expressed as metal. The preferred promoter is potassium and the preferred amount deposited on the support is an amount corresponding to about 0.8 to 2% by weight expressed as metal. I is believed that the promoter will generally be under the form of an oxide on the support rather than under its metallic form.

The promoter can be deposited on the support in accordance with any suitable method such as impregnation. It is however preferred to deposit the promoter, preferably potassium, by impregnation of the support with an aqueous solution of its nitrate.

The so-impregnated support is submitted to a calcination at a temperature between about 380° and about 550° C. in order to decompose the nitrate and to fix the oxide of alkali or alkaline-earth metal on the support. Generally the calcination is carried out in air during about 3 to 7 hours.

According to the present invention, it is preferred that the metal of the platinum group be finally deposited on the so-formed support in an amount sufficient to have a total content of said metal on the support between about 0.1 and 2% by weight, preferably between about 0.2 and 1% by weight. The deposit of this metal can be carried out by means of any suitable technique such as impregnation. However at this stage of treatment of the support, the removal of the compounds which have already been deposited thereon must be avoided. For this purpose, the Applicants have found that for this second impregnation of the metal of the platinum group, it is preferable to use an aqueous solution of a complex of platinum having the general formula $(Pt\ L_2)X_2$, $(Pt\ L_2)X_4$ or $(Pt\ L_4)X_2$, wherein L represents a ligand selected from $NH_3$, $R-NH_2$ or $NH_2$-$R-NH_2$, with R being a hydrocarbon radical having from 2 to 6 carbon atoms, preferably from 2 to 4 carbon atoms, and wherein X represents $NO_3$ or a halogen. An aqueous solution of the amminated complex having the formula $(Pt(NH_3)_4)Cl_2$ is most preferably used.

After this impregnation, the newly impregnated support is dried then submitted to a calcination in air, preferably at a temperature between about 450° and 525° C. during about 10 to 20 hours.

According to the present invention, the so-prepared catalyst can be used in the dehydrogenation process without necessitating the use of other promoters to increase the stability or the selectivity, but it is understood that the usual promoters can be added without departing from the scope of the present invention.

According to a preferred process of the invention, a feed of a paraffinic hydrocarbon having from 3 to 6 carbon atoms, more preferably propane, is contacted with the catalyst as hereinabove described, under dehydrogenation operating conditions. This process can be carried out in a fixed bed reactor or a mobile bed reactor or even a fluidized bed reactor; the process is preferably carried out under continuous conditions, although it can also be carried out in batch. The hydrocarbon feed can be treated in the liquid form, or in a liquid-vapor phase or also in the vapor phase.

The dehydrogenation process is preferably carried out in the vapor phase, at a temperature between about 400° and about 800° C., at a pressure between about 0.01 and 10 atm. and at a weight hourly space velocity (WHSV) between about 0.1 and 21.

More preferably, when propane is used as the feed, the temperature is between about 530° and 650° C., the pressure is between about 0.5 and 3 atm. and the WHSV is between about 1 and about 10.

The feed can be diluted with usual gaseous diluents, under molar ratios more preferably between about 1 and 10 moles of diluent per mole of feed. As diluent, $N_2$, $CO_2$ and $H_2O$ are the most preferred.

The Applicants have also found that it is more preferable to co-feed hydrogen with the feed under molar ratios generally between about 0.05 and 0.5 mole of hydrogen per mole of feed, whether or not the feed is also diluted with gaseous diluents.

The effluent from the dehydrogenation zone contains a part of unconverted feed, hydrogen and dehydrogenation products. This effluent is first cooled and sent into a separator to separate hydrogen and to recover a liquid phase rich in dehydrogenated hydrocarbon. This latter phase is then submitted to a series of separations in order to recover the desired product, i.e. propylene when propane is dehydrogenated, and to recycle the unconverted phase to the reactor.

The catalyst prepared according to the process of the present invention can equally be used for the dehydrocyclization of straight chain hydrocarbons preferably having at least 6 carbon atoms capable of being cyclized. The preferred hydrocarbons are n-alkanes, however, the use of olefins is also possible. The more preferred paraffins are those having 6 to 10 carbon atoms that will produce benzene and/or alkyl substituted benzenes that will have a minimum of secondary reactions.

The dehydrocyclization in the presence of the catalyst of the present invention can be conducted under the following conditions:
Temperature: 300° to 360° C.
Pressure: 1 to 90 bars
LHSV: 0.1 TO 20

The following examples are given to better illustrate the process of the invention but without limiting its scope.

EXAMPLE 1

Preparation of the catalyst.

A 99.8% purity alumina having a specific area of 189 $m^2/g$ and a pore volume of 0.94 ml/g was used.

This alumina was first impregnated with an aqueous solution of $SnCl_2$. The impregnation was carried out in order to obtain a tin final content of 0.49% by weight. After this impregnation the support was calcined at 500° C. during 18 hours.

The tin containing support was then impregnated with a solution of $H_2PtCl_6$ in order to deposit about 0.15% platinum on the support. The support was then submitted to a further calcination at 500° C. during 18 hours. The support was left in the oven at 500° C. and hydrogen was passed over the support during 1 hour in order to carry out a reduction.

The so-impregnated support was then treated with a solution of potassium nitrate in order to deposit thereon 1.00% by weight potassium, expressed as metal.

After this impregnation, the support was then submitted to a calcination to fix the oxide of the alkali metal on the support; this calcination was carried out in air at 400° C. during 5 hours.

Finally, the second impregnation of the support with a platinum compound was carried out to obtain a platinum final content of 0.40% by weight. To carry out this impregnation the support was contacted with an aqueous solution of platinum amminated complex of the formula $(Pt(NH_3)_4)Cl_2$. After the impregnation the support was calcined in air at 500° C. during 18 hours.

A propane feed was dehydrogenated by passing it through a reactor in the presence of the catalyst hereinabove prepared, and under the following operating conditions:
Temperature: 600° C.
Pressure: 1.1 atm.
WHSV: 3

Hydrogen was co-fed with the feed under a molar ratio of 0.1 mole/mole of feed.

Propylene was recovered in the effluent with a yield of 91.1% of the theoretical thermodynamic equilibrium yield under these conditions. By way of comparison, different catalysts were prepared (Table 1).

Catalyst A

Only one impregnation with platinum was carried out

Catalyst B

Only one impregnation with all the catalytic metals and the promoter was carried out Catalyst C A calcination and a reduction were carried out after the impregnation with platinum, but the second impregnation with platinum was not done.

Catalyst D

Platinum has been deposited through two impregnations, but without carrying out any calcination or reduction after the first impregnation.

Catalyst E

Platinum has been deposited on an $Al_2O_3/Sn$ support in a single impregnation, without adding a promoter.

Those catalysts were tested as hereinabove described to dehydrogenate a propane feed in accordance with operating conditions identical to those hereinabove described. The results are indicated in Table II.

TABLE I

| | Composition % | | | Impregnation SnCl w/calcination at 500° F. | 1st Impregnat. Pt | Calcination | Reduction | Impregnat. KNO3 and calcin. at 400° C. | 2nd Impregnat. Pt and calcination |
|---|---|---|---|---|---|---|---|---|---|
| | Sn | Pt | K | | | | | | |
| Cat. A | 1.06 | 0.46 | 0.61 | yes | $H_2PtCl_6$ | 500° C. | no | yes | no |
| Cat. B | 0.9 | 0.53 | 1.1 | only one impregnation with all the catalytic metals and calcination at 500° C. | | | | | |
| Cat. C | 0.4 | 0.26 | 2.35 | yes | $H_2PtCl_6$ | drying 100° C. | yes | yes | no |
| Cat. D | 1.01 | 0.83 | 2.11 | yes | $H_2PtCl_6$ (no calcination) | drying 100° C. | no | drying 200° C. | $(Pt(NH_3)_4)Cl_2$ |

TABLE I-continued

| | Composition % | | | Impregnation SnCl w/calcination at 500° F. | 1st Impregnat. Pt | Calcination | Reduction | Impregnat. KNO$_3$ and calcin. at 400° C. | 2nd Impregnat. Pt and calcination |
|---|---|---|---|---|---|---|---|---|---|
| | Sn | Pt | K | | | | | | |
| Cat. E | 0.98 | 0.49 | 0 | yes | H$_2$PtCl$_6$ | 500° C. | no | no | no |

TABLE II

| | Yield/Theor. Yield | Selectivity |
|---|---|---|
| Cat. A | 60% | 96.7% |
| Cat. B | 72% | 91.0% rapidly deactivating after 8 h |
| Cat. C | 83% | 95.9% |
| Cat. D | 60% | 96.7% |
| Cat. E | 69% | 93.0% |

EXAMPLE 2

Different catalysts were prepared in accordance with the method of the invention (see Table III) with an alumina identical to that of Example 1.

TABLE III

| | Composition % | | | Impregnation SnCl$_2$ + Calc. 500° C. | Impregnation Pt | Calcination | Reduction |
|---|---|---|---|---|---|---|---|
| | Pt | Sn | K | | | | |
| 2 | 0.17 | 0.94 | 1.24 | yes | H$_2$PtCl$_6$ | 500° C. | 1 h/500° C. |
| 3 | 0.74 | 1.00 | 1.9 | yes | H$_2$PtCl$_6$ | 480° C. | 1 h/500° C. |
| 4 | 0.4 | 0.49 | 1.00 | yes | H$_2$PtCl$_6$ | 520° C. | 1 h/500° C. |
| 5 | 0.83 | 0.95 | 1.41 | yes | H$_2$PtCl$_6$ | 500° C. | 1 h/500° C. |

| | Impregnation | Calcination | 2nd Impregnation | Calcination |
|---|---|---|---|---|
| 2 | yes | 400° C. | (Pt(NH$_3$)$_4$)Cl$_2$ | 500° C./18 h |
| 3 | yes | 370° C. | (Pt(NH$_3$)$_4$)Cl$_2$ | 520° C./16 h |
| 4 | yes | 410° C. | (Pt(NH$_3$)$_4$)Cl$_2$ | 500° C./20 h |
| 5 | yes | 400° C. | (Pt(NH$_3$)$_4$)Cl$_2$ | 500° C./18 h |

These catalysts were used for the dehydrogenation of a propane feed in accordance with the following operating conditions.

T: 600° C.
Pressure: 1.1 atm (0.11 Mpa)
WHSV: 3
H$_2$/HC: 0.1 mole/mole (HC = hydrocarbons)

The results obtained with these catalysts are indicated in the following table.

TABLE IV

| Examples | Yield/Theory | Selectivity |
|---|---|---|
| 2 | 95.1% | 97.1% |
| 3 | 88.6% | 97% |
| 4 | 92.8% | 98.5% |
| 5 | 95.3% | 97.2% |

EXAMPLE 6

The catalyst as prepared in Example 4 was used for the dehydrogenation of an n-butane feed under the following operating conditions.

T: 630° C.
Pressure: 2 atm (0.2 MPa)
WHSV: 5
H$_2$/HC: 0.4

The results obtained were the following:

| Yield/Theory | Selectivity |
|---|---|
| 72% | 94.5% |

When a catalyst prepared as in the comparative example 1A was used, a yield of only 48% was obtained with a selectivity of only 93.6%.

What is claimed is:

1. A process for the catalytic dehydrogenation of paraffinic hydrocarbons having from 3 to 6 carbon atoms, in the presence of a catalyst comprising an alumina support containing at least one metal from the platinum group together with a co-catalyst and a promoter comprising the step of passing the feed to be dehydrogenated onto a catalyst containing from 0.1 to 2% by weight of at least one metal from the platinum group, from 0.1 to 2% by weight of at least one metal from the tin group as co-catalyst and from 0.5 to 5% by weight of at least one alkali or alkaline-earth metal as promoter, said catalyst being obtained by submitting the alumina support, containing the co-catalyst and calcined at a temperature comprised between about 450° and about 550° C.,
to a first treatment with a metal compound of the platinum group, said first treatment being followed by a calcination in air and by a reduction in the presence of hydrogen at a temperature between about 450° and 550° C.;
then to an intermediate treatment to deposit the promoter, said intermediate treatment being followed by a calcination at a temperature between about 380° and about 550° C.;
and finally to a second treatment with a metal compound of the platinum group, said second treatment being followed by a calcination at a temperature not exceeding 525° C.,
the dehydrogenation being carried out in the presence of said catalyst at a temperature between about 400° and 800° C., under a pressure between about 0.001 and 10 atm and at a weight hourly space velocity between about 0.1 and 21.

2. The process according to claim 1 wherein the catalyst contains about 0.15 to 1% by weight of a metal of the tin group, and about 0.8 to 2.5% by weight of an alkali or alkaline-earth metal.

3. The process according to claim 1 wherein the metal of the group is platinum.

4. The process according to claim 1 wherein the second treatment with the metal of the platinum group is carried out with a compound of the formula (Pt $L_2)X_2$, $(Pt\ L_2)X_4$ or $(Pt\ L_4)X_2$ wherein L represents a ligand selected from the group comprising $NH_3$, $R-NH_2$ or $NH_2-R-NH_2$, with R being a hydrocarbon radical having from 2 to 4 carbon atoms and wherein X is $NO_3$ or a halogen.

5. The process according to claim 4, wherein $(Pt(NH_3)_4)Cl_2$ is used as platinum compound for the second treatment step.

6. The process according to claim 1 wherein the promoter is potassium.

7. The process according to claim 1, wherein 05 to 0.5 mole of hydrogen is co-fed with each mole of paraffinic hydrocarbon.

8. The process for the catalytic dehydroqenation of propane, in the presence of hydrogen in a molar ratio of from 0.05 to 0.5 mole of hydrogen per mole of propane over a catalyst comprising an alumina support containing at least one metal of the platinum group together with a co-catalyst and a promoter, which comprises the step of passing the feed to be dehydrogenated onto a catalyst containing from 0.2 to 1% by weight of platinum, from 0.15 to 1% by weight of tin as co-catalyst and from 0.8 to 2% by weight of potassium as promoter, said catalyst being obtained by submitting the alumina support containing the co-catalyst and calcined at a temperature between 450° and 550° C., to a first treatment with a platinum compound, said first treatment being followed by a calcination in air and a reduction in the presence of hydrogen at a temperature between 450° and 550° C.;

then to an intermediate treatment to deposit potassium, said intermediate treatment being followed by a calcination at a temperature between 380° and 550°, and finally to a second treatment with a platinum compound, said second treatment being followed by a calcination at a temperature not exceeding 525° C., the dehydrogenation being carried out in the presence of said catalyst at a temperature between 530° C. and 650° C., a pressure between 0.5 and 3 atm, and a weight hourly space velocity between 1 and 10.

* * * * *